United States Patent [19]

Inouye et al.

[11] 4,203,768
[45] May 20, 1980

[54] SILVER HALIDE COLOR PHOTOGRAPHIC MATERIAL AND METHOD FOR FORMATION OF COLOR PHOTOGRAPHIC IMAGES

[75] Inventors: Kozo Inouye; Hideki Naito, both of Minami-ashigara, Japan

[73] Assignee: Fuji Photo Film Co., Ltd., Minami-ashigara, Japan

[21] Appl. No.: 945,946

[22] Filed: Sep. 26, 1978

[30] Foreign Application Priority Data

Sep. 26, 1977 [JP] Japan .................................... 52-115265

[51] Int. Cl.$^2$ .......................... G03C 7/00; G03C 1/40
[52] U.S. Cl. .................................... 430/388; 430/376; 430/380; 430/470; 430/505
[58] Field of Search .................. 96/100 R, 100 N, 55, 96/56.2, 56.6, 74, 56.4, 56.5

[56] References Cited

U.S. PATENT DOCUMENTS

| | | | |
|---|---|---|---|
| 3,933,501 | 1/1976 | Cameron et al. | 96/74 |
| 3,960,570 | 6/1976 | Oishi et al. | 96/100 |
| 3,990,896 | 11/1976 | Arai et al. | 96/100 N |
| 4,022,620 | 5/1977 | Okumura et al. | 96/100 |
| 4,095,983 | 6/1978 | Wolff et al. | 96/100 |
| 4,106,942 | 8/1978 | Tanaka et al. | 96/100 N |

Primary Examiner—J. Travis Brown
Attorney, Agent, or Firm—Sughrue, Rothwell, Mion, Zinn and Macpeak

[57] ABSTRACT

A silver halide color photographic material comprising a photographic silver halide emulsion containing a yellow dye-forming coupler represented by the following general formula (I) or (II):

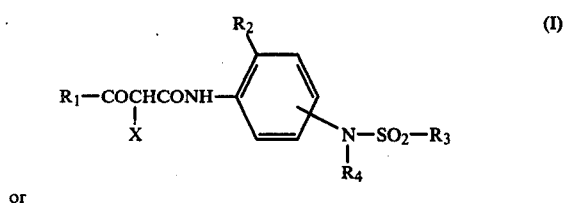

wherein $R_1$ represents an alkyl group or an aryl group; $R_2$ represents a chlorine atom or a lower alkoxy group having 1 to 4 carbon atoms; $R_3$ and $R_4$, which may be the same or different, each represents an alkyl group having 1 to 22 carbon atom, a phenoxyalkyl group having 7 to 32 carbon atoms, a monocyclic aralkyl group or a phenyl group, a phenyl group which is substituted with an alkoxy group, an alkyl group, an acyl group, or an alkoxycarbonyl group; and X is selected from the group consisting of groups represented by the following general formulae (III) to (V):

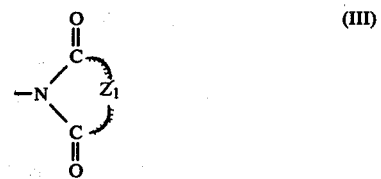

wherein $Z_1$ represents the non-metallic atoms necessary to form together with the

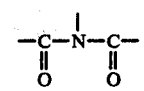

moiety a 5-membered ring or a 6-membered ring,

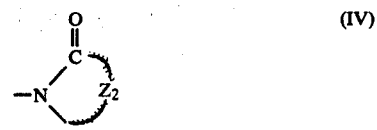

wherein $Z_2$ represents the non-metallic atoms necessary to form together with the

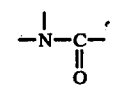

moiety an unsaturated 5-membered ring or an unsaturated 6-membered ring, or

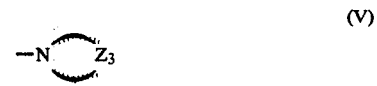

wherein $Z_3$ represents the non-metallic atoms necessary to form together with

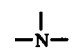

an imidazole ring, a triazole ring or a tetrazole ring.

9 Claims, No Drawings

SILVER HALIDE COLOR PHOTOGRAPHIC MATERIAL AND METHOD FOR FORMATION OF COLOR PHOTOGRAPHIC IMAGES

BACKGROUND OF THE INVENTION

1. Field of the Invention

The present invention relates to a coupler-containing photographic silver halide emulsion and a method for the formation of color photographic images using a coupler and, more particularly, to a photographic silver halide emulsion containing a novel yellow color-forming coupler and to a method for the formation of color photographic images.

2. Description of the Prior Art

In the formation of color images in subtractive color photography, an aromatic primary amine compound, especially an N,N-disubstituted p-phenylenediamine compound, is used as a developing agent, to reduce the silver halide grains in an exposed photographic silver halide emulsion, and the concurrently produced oxidation product of the developing agent reacts with the coupler to form a cyan, magenta or yellow dye image.

The couplers used in the above-described color photographic process have a phenolic hydroxy group, an anilinic amino group or an active methylene group, and, by oxidative coupling with the aromatic primary amine developing agent, form dyes which absorb light in the visible wavelength range.

Yellow dye images show a specific absorption to blue light in wavelengths ranging from about 400 to 500 millimicrons. Previously known yellow-forming color couplers include $\beta$-ketoacetoacetic acid esters, $\beta$-diketones, N,N-malonic diamides and $\alpha$-acylacetamides, of which the $\alpha$-acylacetamides have been widely used as advantageous yellow color-forming couplers in the field of color photography.

The $\alpha$-acylacetamides as couplers and the yellow dyes derived therefrom as images have, however, a number of disadvantages and are by no means completely satisfactory. For example, conversion of the $\alpha$-acylacetamides to the azomethine dyes require 4 equivalents of silver halide as the oxidizing agent, per molecule, and, moreover, the maximum molecular extinction coefficient of the dyes formed is only on the order of about 20,000 liter/mol·cm.

Many investigations have been made in order to improve these disadvantages. For example, $\alpha$-acylacetanilides wherein one of the hydrogen atoms of the active methylene group is replaced by a halogen atom, such as fluorine or chlorine, a sulfoxy group, an acyloxy group, etc., as described in U.S. Pat. Nos. 3,369,895, 3,408,194, 3,415,652 and 3,447,928 were developed for the purpose of reducing the amount of silver halide necessary in a light-sensitive material and improving the coupling reactivity. However, these couplers have the disadvantages that the coupling reactivity is still insufficient, a marked color fog is produced, the couplers per se are unstable or the fastness of the color images formed therefrom is insufficient.

As the result of further investigations to overcome these disadvantages, couplers in which one of the hydrogen atoms of the active methylene group is replaced with an imido group as described in British Pat. No. 1,386,151, and the couplers as described in U.S. Pat. No. 3,894,875, have been developed. However, these couplers are also still insufficient from the standpoint of coupling reactivity and the fastness of the dye images formed. Furthermore, couplers capable of being used to produce images of high quality, such as sharpness, graininess, etc., and also having a high coupling reactivity are required, in particular, in light-sensitive materials having high speed, such as color negative or color reversal light-sensitive materials for taking photos. However, these properties of the above-described couplers are also insufficient.

Still further, the couplers described in German Patent Application (OLS) No. 2,556,620 are still insufficient from the standpoint of coupling reactivity and properties for providing images of excellent image quality, such as sharpness, graininess, etc.

SUMMARY OF THE INVENTION

Therefore, a first object of the present invention is to provide a novel yellow color-forming coupler suitable for color photography by a subtractive color reproduction process.

A second object of the present invention is to provide a method for formation of dye images by developing an image-wise exposed silver halide emulsion in the presence of a novel yellow color-forming coupler.

A third object of the present invention is to provide a color light-sensitive material comprising a support having thereon a layer of a silver halide emulsion containing a novel yellow color-forming coupler.

A fourth object of the present invention is to provide a color developer solution containing a novel yellow color-forming coupler.

A fifth object of the present invention is to provide a means for reducing the amount of silver halide which must be present in a photographic emulsion and improving the sharpness of the images formed by the use of a novel yellow color-forming coupler.

A sixth object of the present invention is to provide a means for improving the graininess of the images formed by the use of a novel yellow color-forming coupler.

A seventh object of the present invention is to provide a photographic light-sensitive material which is well suited for use in rapid processing at a high temperature using a novel yellow color-forming coupler.

An eighth object of the present invention is to provide yellow dye images having good stability using a novel yellow color-forming coupler.

It has now been found that the above-described objects are accomplished with a yellow dye-forming coupler represented by the following general formula (I) or (II):

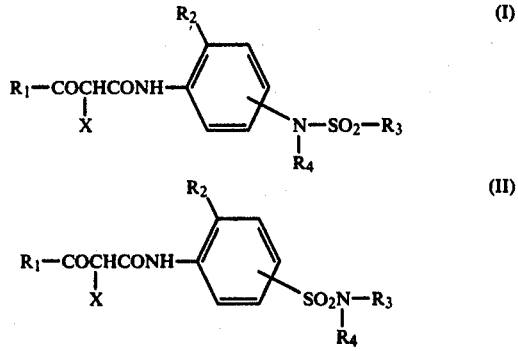

wherein $R_1$ represents an alkyl group (for example, a branched chain alkyl group having 3 to 8 carbon atoms which may be substituted with an alkoxy group, such as a methoxy group, etc., or an aryloxy group, such as a phenoxy group, etc., e.g., an isopropyl group, a tert-butyl group, a tert-amyl group, a 2-hexadecyloxypropan-2-yl group, a 2-phenoxypropan-2-yl group, etc.; and a cyclic alkyl group having 3 to 10 carbon atoms, such as an adamantyl group, etc.) or a monocyclic aryl group (for example, a phenyl group, a 2- or 4-alkylphenyl group or a 2- or 4-alkoxyphenyl group, etc., wherein the alkyl moiety in the aryl group is a straight chain alkyl group having 1 to 5 carbon atoms, such as a methyl group, an ethyl group, a butyl group, etc., or a branched chain alkyl group having 1 to 5 carbon atoms, such as an isopropyl group, a t-butyl group, etc.; and the alkoxy moiety in said aryl group is a straight chain alkoxy group having 1 to 5 carbon atoms, such as a methoxy group, an ethoxy group, a butoxy group, etc., or a branched chain alkoxy group having 1 to 5 carbon atoms, such as an isopropoxy group, a t-butoxy group, etc.); $R_2$ represents a chlorine atom or a straight chain lower alkoxy group having 1 to 4 carbon atoms, such as a methoxy group, an ethoxy group, etc., or a branched chain lower alkoxy group having 1 to 4 carbon atoms, such as a t-butoxy group, etc.; $R_3$ and $R_4$, which may be the same or different, each represents a straight chain alkyl group having 1 to 22 carbon atoms, such as a methyl group, an n-octyl group, an n-hexadecyl group, etc.; a branched chain alkyl group having 1 to 22 carbon atoms, such as an isopropyl group, an isooctyl group, etc.; a phenoxyalkyl group having 7 to 32 carbon atoms wherein the alkyl moiety is a straight chain alkyl group, such as an n-propyl group, an n-amyl group, an n-pentadecyl group, etc., or a branched chain alkyl group, such as an ethylmethyl group, a t-amyl group, a t-hexyl group, etc.; a monocyclic aralkyl group having 7 to 32 carbon atoms which may be substituted with an alkyl group having 1 to 20 carbon atoms, such as a methyl group, an octadecyl group, etc., or an alkoxy group having 1 to 20 carbon atoms, such as a methyloxy group, an octadecyloxy group, etc., wherein the alkyl moiety of the alkyl group is a straight chain alkyl group, such as a methyl group, a propyl group, etc.; a phenyl group or a phenyl group substituted with an alkoxy group having 1 to 20 carbon atoms, such as an octyloxy group, a hexadecyloxy group, etc., an alkyl group having 1 to 20 carbon atoms, such as a nonyl group, a dodecyl group, etc., an acyl group having 1 to 20 carbon atoms, such as a hexanoyl group, an octadecanoyl group, etc., or an alkoxycarbonyl group having 1 to 20 carbon atoms in the alkyl moiety, such as a hexyloxycarbonyl group, a hexadecanyloxycarbonyl group, etc. (for example, octyloxyphenyl, nonylphenyl, octadecanoylphenyl, hexyloxycarbonylphenyl, etc.); and X is selected from the group consisting of groups represented by the following general formulae (III) to (V):

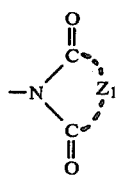

(III)

wherein $Z_1$ represents the non-metallic atoms necessary to form together with the

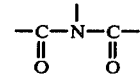

moiety a 5-membered ring or a 6-membered ring,

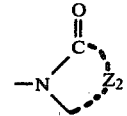

(IV)

wherein $Z_2$ represents the non-metallic atoms necessary to form together with the

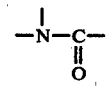

moiety an unsaturated 5-membered ring or an unsaturated 6-membered ring, and

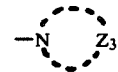

(V)

wherein $Z_3$ represents the non-metallic atoms necessary to form together with

an imidazole ring, a triazole ring or a tetrazole ring.

Suitable examples of the ring represented by the general formula (III) include a hydantoinyl group, an oxazolidinedionyl group, a urazolyl group, etc. Suitable examples of the ring represented by the general formula (V) include a 1,2,4-triazolyl group, etc. Most of the above-described hydantoins, oxazolidines and urazoles are commercially available and the rest are described in U.S. Pat. No. 4,022,620 and *J. Heterocyclic Chemistry*, p. 897 (1971).

DETAILED DESCRIPTION OF THE INVENTION

Of the groups represented by the general formula (III), the groups which are described as releasable groups for 2-equivalent yellow couplers disclosed in, for example, British Pat. Nos. 1,386,151, 1,421,126 and 1,425,020, U.S. Pat. Nos. 4,012,259, 4,057,432, 3,990,896, and 4,022,620, French Pat. No. 2,134,506 and German Patent Application (OLS) No. 2,261,361, etc., are particularly preferred.

Of the groups represented by the general formula (IV), the groups which are described as releasable groups for 2-equivalent yellow couplers disclosed in, for example, British Pat. Nos. 1,402,511, 1,478,205, and 1,476,760, and German Patent Application (OLS) No. 2,363,675 are particularly preferred.

Of the groups represented by the general formula (V), the imidazole groups and triazole groups which are described as releasable groups for 2-equivalent yellow couplers disclosed in U.S. Pat. No. 3,933,500 and British Pat. No. 1,476,760 and the triazole groups represented by the following general formula (VI) and tetrazole groups are particularly preferred.

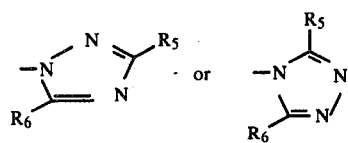
(VI)

wherein $R_5$ and $R_6$, which may be the same or different, each represents a hydrogen atom, an alkyl group having 1 to 8 carbon atoms (for example, methyl, ethyl, isobutyl, butyl, β-ethoxyethyl, octyl, etc.), a monocyclic aryl group having 6 to 15 carbon atoms which may be substituted with an alkyl group having 1 to 10 carbon atoms, such as a methyl group, an octyl group, etc. (for example, phenyl, tolyl, anisyl, chlorophenyl, carboxyphenyl, etc.), a benzyl group, an amino group, an alkylamino group having 1 to 10 carbon atoms (for example, methylamino, octylamino, etc.), a monocyclic arylamino group having 6 to 15 carbon atoms (for example, anilino, etc.), a straight chain alkoxycarbonyl group having 2 to 11 carbon atoms (for example, methoxycarbonyl, ethoxycarbonyl, etc.), a halogen atom (for example, fluorine, chlorine, etc.), a straight chain acylamino group having 1 to 10 carbon atoms in the alkyl moiety (for example, acetylamino, tert-butanamido, chloroacetylamino, trifluoroacetylamino, etc.) or a sulfonamido group (for example, a straight chain alkylsulfonamido group having 1 to 10 carbon atoms, such as methanesulfonamido, etc., and a monocyclic arylsulfonamido group, such as phenylsulfonamido, etc.).

Yellow color-forming couplers of the above-described general formula (I) or (II) in which the

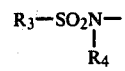

group or the

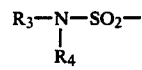

group is bonded at the para-position to $R_2$ are preferred. Yellow color-forming couplers of the above-described general formula (I) are most preferred since they are highly effective.

Particularly preferred yellow color-forming couplers of the general formulae (I) and (II) which can be used in the present invention are those couplers represented by the following general formula (VII):

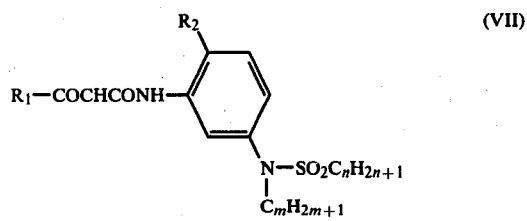
(VII)

wherein $R_1$, $R_2$ and X each has the same meaning as defined in the general formula (I) or (II), and m and n each represents an integer of 1 to 18.

Typical examples of yellow color-forming couplers which can be used in the present invention are illustrated below. However, the present invention is not to be construed as being limited to these examples.

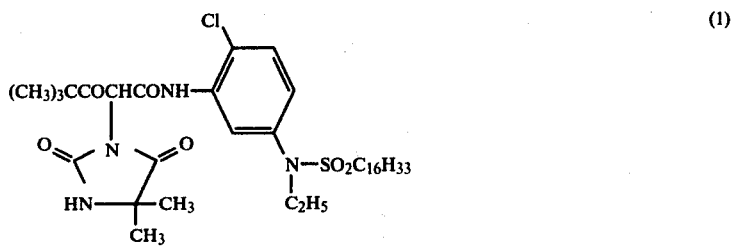
(1)

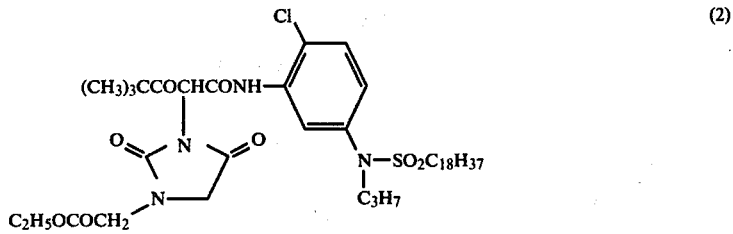
(2)

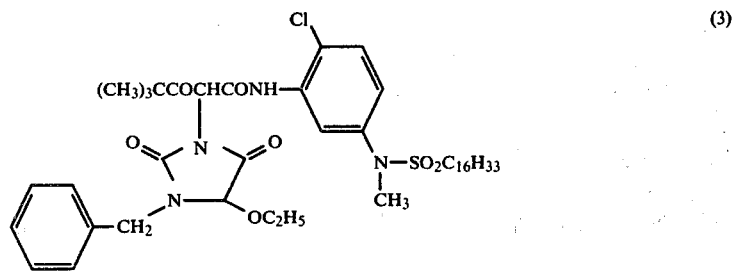
(3)

(4)
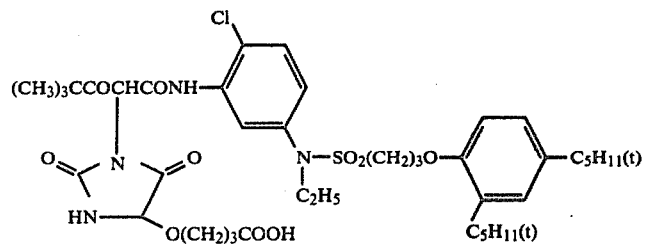
(5)
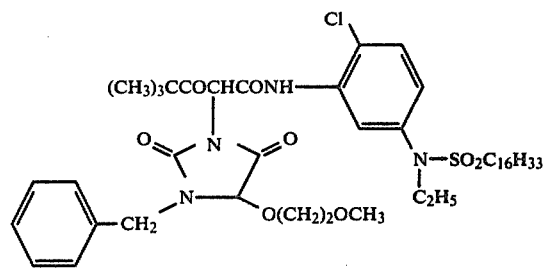
(6)
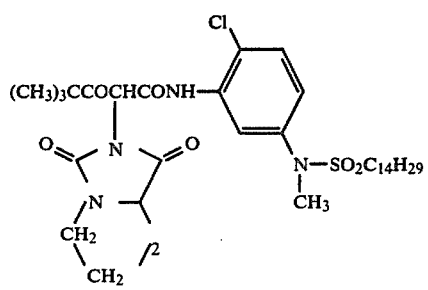
(7)
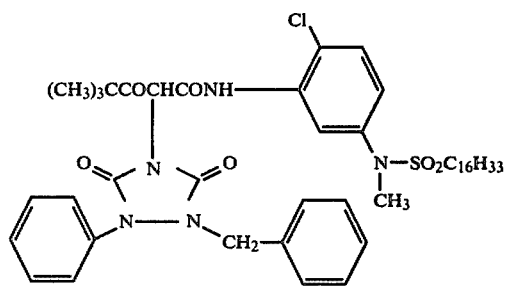
(8)
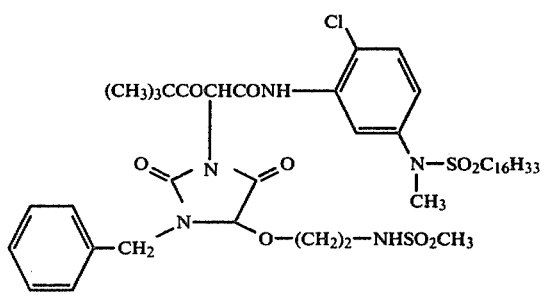
(9)
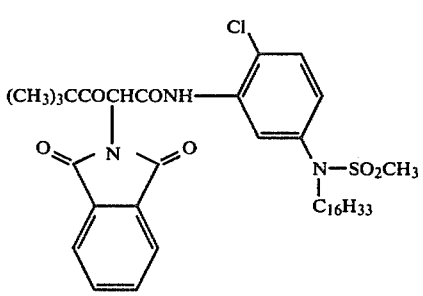

-continued
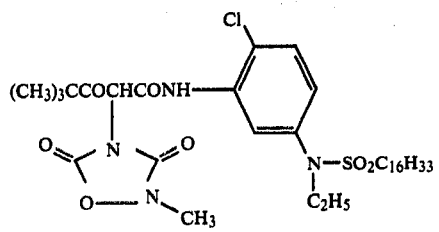 (10)
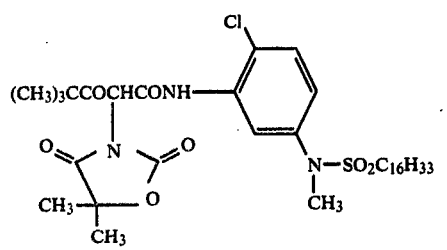 (11)
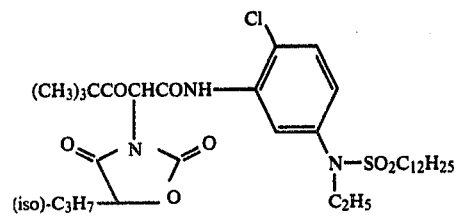 (12)
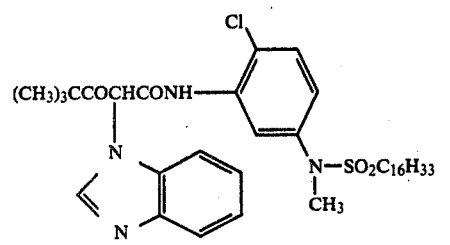 (13)
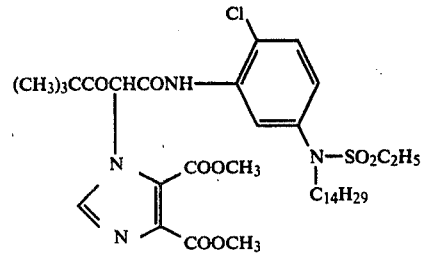 (14)
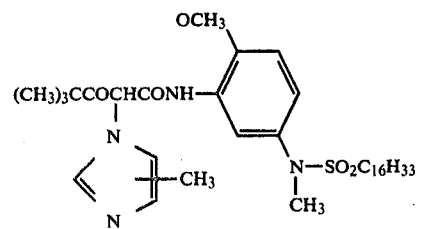 (15)
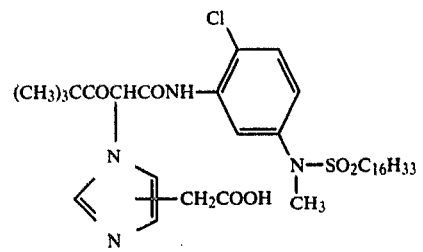 (16)

-continued
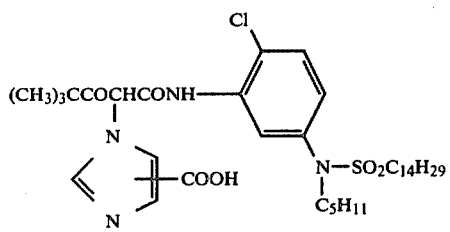
(17)
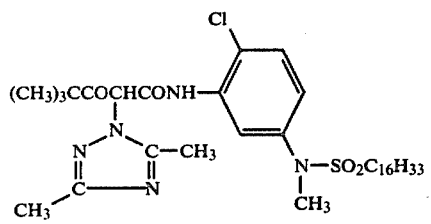
(18)
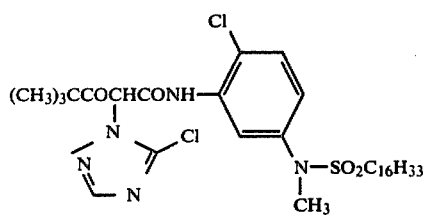
(19)
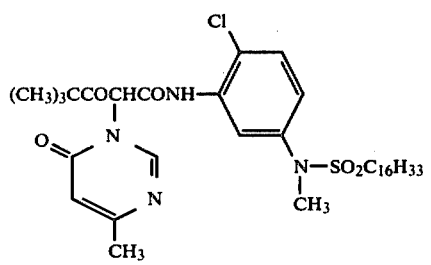
(20)
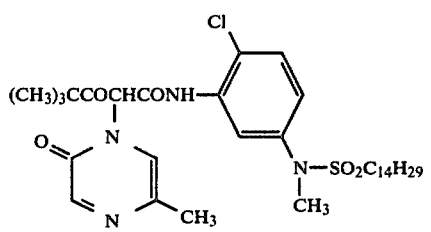
(21)
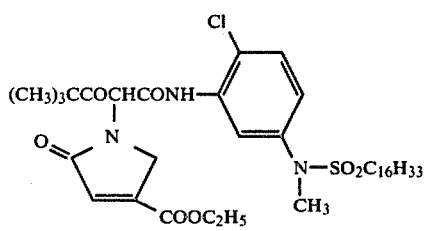
(22)
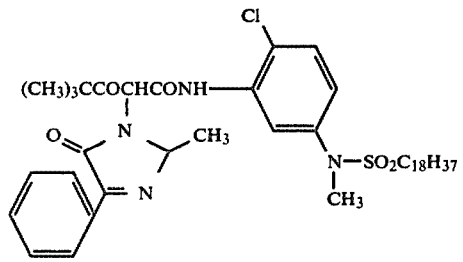
(23)

-continued
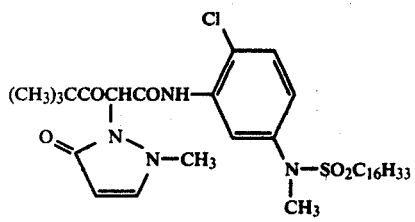
(24)
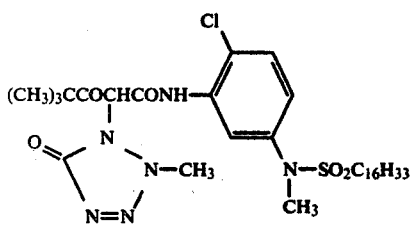
(25)
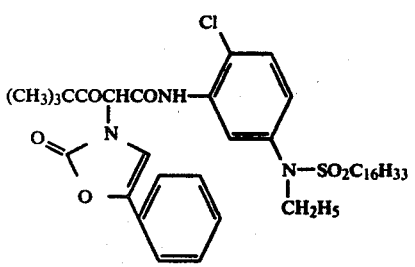
(26)
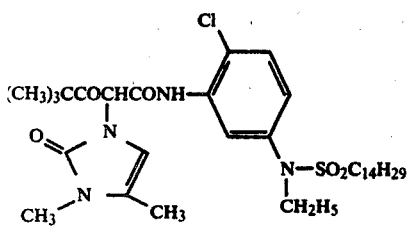
(27)
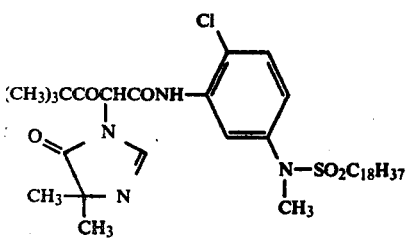
(28)
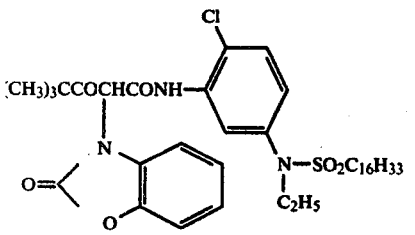
(29)
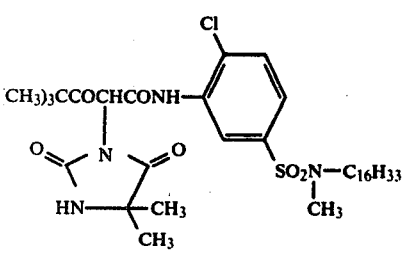
(30)

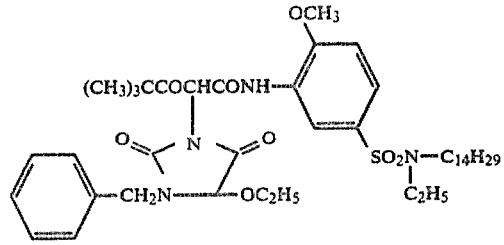
(31)
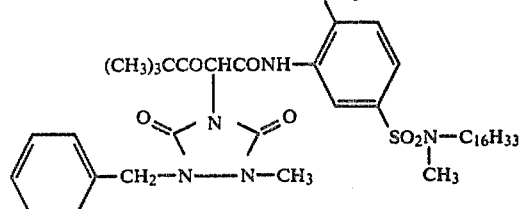
(32)
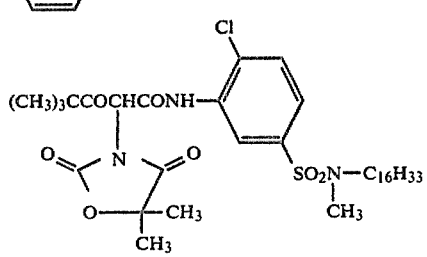
(33)
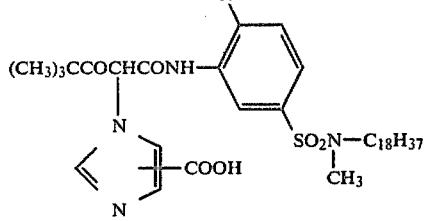
(34)
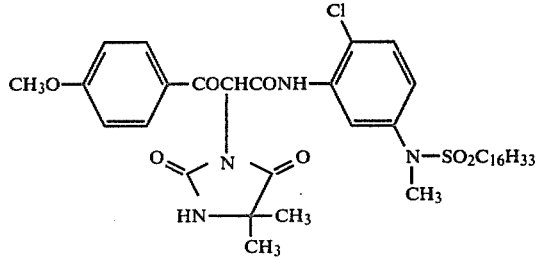
(35)
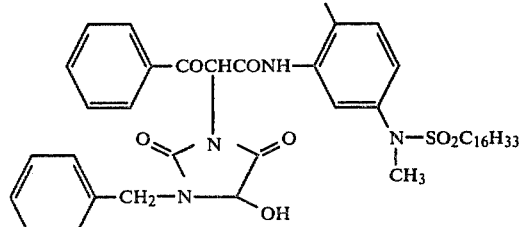
(36)
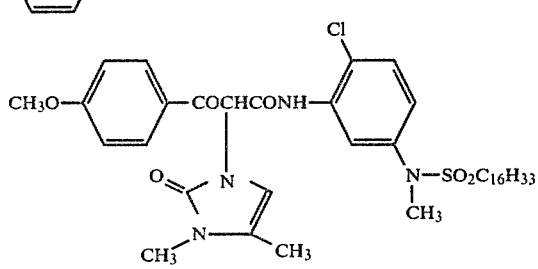
(37)

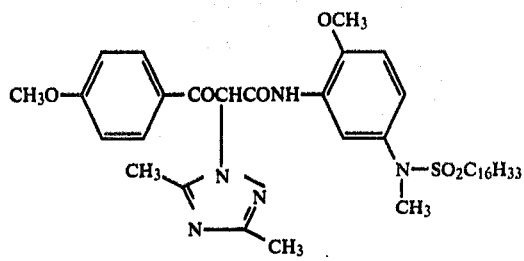

(38)

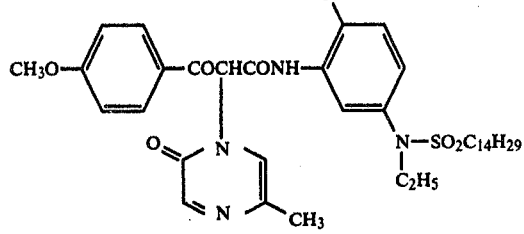

(39)

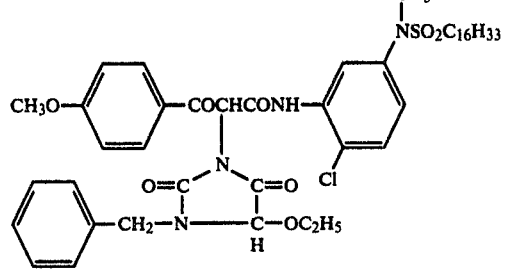

(40)

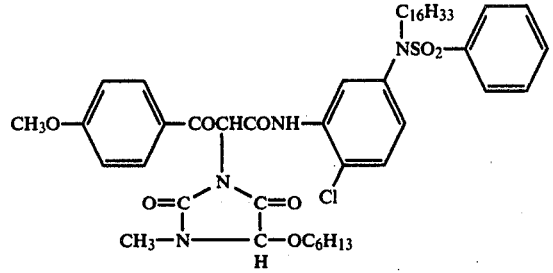

(41)

The light-sensitive photograhic material containing the coupler according to the present invention provides particularly improved graininess and sharpness in comparison with a light-sensitive photographic material containing a known coupler.

The coupler of the present invention can be generally prepared by halogenating a 4-equivalent mother coupler (where Y=H in the following general formula (VIII)) with a halogenating agent, such as $Br_2$, $Cl_2$, $SO_2Cl_2$, etc., in an amount of from about 0.9 to about 1.2 mols per mol of the mother coupler to form a halogenated compound (where Y=Cl or Br in the following general formula (VIII)) and reacting the halogenated compound with a corresponding compound of the formula X—X (where X is the same as defined in the general formula (I)) in an amount of from about 1 to about ½ mol per mol of H—X (as defined above) in the presence of a solvent, such as $CH_2Cl_2$, $CHCl_3$, dimethylformamide, etc., at a temperature of from about 0° to about 40° C.

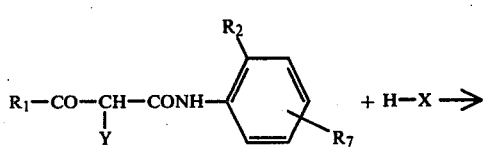

(VIII)

(IX)

wherein $R_1$ and $R_2$ each has the same meaning as defined in the general formulae (I) and (II), and $R_7$ represents

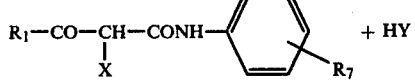

for producing compounds of the general formula (I) or

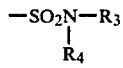

for producing compounds of the general formula (II).

The 4-equivalent mother coupler used as a starting material can be prepared, for example, according to the method as described in *J. Amer. Chem. Soc.*, Vol. 59, page 1837 (1937).

Typical synthesis examples of couplers of the present invention are specifically illustrated below. Unless otherwise indicated, all parts, percents, ratios and the like are by weight.

SYNTHESIS EXAMPLE 1

Synthesis of
α-Pivaloyl-α-(5-ethoxy-1-benzyl-3-hydantoinyl)-2-chloro-5-N-methyl-hexadecanesulfonamidoacetanilide [Coupler (3)]

Synthesis of Intermediate A: 2-Chloro-5-N-methylhexadecanesulfonamidoaniline

Hexadecanesulfonylchloride, which was prepared by the method as described in J. M. Sprague, et al., *J. Amer. Chem. Soc.*, Vol. 59, page 1837 (1937), was reacted with 2-chloro-5-aminonitrobenzene in a chloroform solution in the presence of pyridine to prepare 2-chloro-5-hexadecanesulfonamidonitrobenzene.

115 g of the 2-chloro-5-hexadecanesulfonamidonitrobenzene thus-prepared was dissolved in 500 ml of chloroform and an equimolar amount (43 g) of methyl iodide, a catalytic amount (8.3 g) of tetrabutylammonium bromide and 10 times on a molar basis of a 30% aqueous sodium hydroxide solution were added to the solution. The mixture was stirred vigorously to prepare 2-chloro-5-N-methyl-hexadecanesulfonamidonitrobenzene.

Then, 20 g of the 2-chloro-5-N-methyl-hexadecanesulfonamidonitrobenzene prepared as described above was dissolved in 500 ml of ethanol and hydrogenated with hydrogen gas (20 atm) using palladium as a catalyst and the reduced compound thus-obtained was recrystallised from methanol, yielding Intermediate A having a melting point of 65° to 66° C.

Synthesis of Intermediate B: α-Pivaloyl-2-chloro-5-N-methyl-hexadecanesulfonamidoacetanilide By refluxing 1,000 ml of a xylene solution containing 93 g of Intermediate A and 43 g of ethyl pivaloylacetate, Intermediate B was obtained. The melting point of Intermediate B was 50° to 51° C. (recrystallized from methanol).

Synthesis of Coupler (3)

28.5 g of Intermediate B was reacted with an equimolar amount of sulfuryl chloride in 100 ml of chloroform to prepare α-pivaloyl-α-chloro-2-chloro-5-N-methyl-hexadecanesulfonamidoacetanilide. 10 g of the α-pivaloyl-α-chloro-2-chloro-5-N-methyl-hexadecanesulfonamidoacetanilide was reacted with 50 ml of a dimethylformamide (DMF) solution containing 1.5 times on a molar basis of 5-ethoxy-1-benzylhydantoin in the presence of 1.5 times on a molar basis of potassium hydroxide (methanol solution) at room temperature (25° C.) to yield Coupler (3) which was an oily product.

SYNTHESIS EXAMPLE 2

Synthesis of
α-Pivaloyl-α-(5,5-dimethyl-1,3-oxazolidine-2,4-dion-3-yl)-2-chloro-5-N-methyl-hexadecanesulfonamidoacetanilide [Coupler (11)]

The procedures of Synthesis Example 1 were repeated using 5,5-dimethyl-1,3-oxazolidine-2,4-dione in place of 5-ethoxy-1-benzylhydantoin and Coupler (11) was obtained. The melting point of Coupler (11) was 86° to 87° C. (recrystallized from methanol).

In order to produce silver halide color photographic light-sensitive materials, the coupler according to the present invention can be used individually or as a mixture of two or more thereof.

In color photographic light-sensitive materials containing the couplers of the present invention, a DIR coupler or a DIR compound, such as those described in U.S. Pat. Nos. 3,632,345, 3,227,554 and 3,379,529, Japanese Patent Application (OPI) Nos. 122335/1974, 34232/1975 and 135310/1975 (The term "OPI" as used herein refers to a "published unexamined Japanese patent application"), etc., a yellow dye-forming coupler, such as those described in German Patent Application (OLS) No. 2,213,461, U.S. Pat. Nos. 3,510,306, 3,644,498 and 3,894,875, etc., a magenta dye-forming coupler, such as those described in U.S. Pat. No. 3,615,506, German Patent Application (OLS) Nos. 2,418,959 and 2,424,467, etc., and a cyan dye-forming coupler, such as those described in U.S. Pat. Nos. 2,474,293, 3,034,892, 3,591,383, 3,311,476 and 3,476,563, etc., can be incorporated.

Suitable silver halide emulsions which can be used in the present invention include emulsions of silver chloride and silver bromide and also those of mixed silver halides, such as silver chlorobromide, silver iodobromide, silver chloroiodobromide, etc.

These silver halide emulsions can be produced using known conventional methods, for example, a single or double jet method, a controlled double jet method, etc.

Furthermore, silver halide grains wherein latent images are formed in the surface thereof or those wherein latent images are formed in the interior thereof can be used in the present invention.

The silver halide emulsion used in the present invention is preferably sensitized with a known chemical sensitizer, for example, sodium thiosulfate, N,N,N'-trimethyl thiourea, aurous thiocyanate complex salt, aurous thiosulfate complex salt, stannous chloride, hexamethylenetetramine, etc.

Fogging nuclei can be formed in the silver halide grains using a reducing agent, such as hydrazine, or a combination of a reducing agent and a gold compound or a labile sulfur compound.

The photographic emulsion used in the color photographic light-sensitive material containing the coupler according to the present invention can be spectrally sensitized to blue, green or red light using a cyanine dye, such as monomethinecyanine, pentamethinecyanine, merocyanine, or carboxyanine dye, individually or in combination, or using a combination of these dyes and a styryl dye, an amino stilbene compound or the like, if desired.

Known stabilizing agents and anti-fogging agents, for example, 4-hydroxy-6-methyl-1,3,3a,7-tetrazaindene, 3-methylbenzothiazole, 1-phenyl-5-mercaptotetrazole or other mercapto compounds, a metal salt, such as KBr, etc., can be used in the photographic emulsion employed in the present invention.

The couplers of the present invention can be dispersed in the photographic emulsion after dissolving them in an organic solvent. Specific examples of processes for dispersing couplers which can be used are described in detail in U.S. Pat. No. 3,676,131. Suitable organic solvents for dissolving the coupler are those which are slightly soluble in water and have a high boiling point (not lower than 200° C.) and including, for example, substituted hydrocarbons, carboxylic acid esters, benzoic acid esters, citric acid esters, carboxylic acid amides, phosphoric acid esters and ethers. Specific examples of these solvents are di-n-butyl phthalate, n-octyl benzoate, o-acetyltributyl citrate, tricresyl phosphate, tri-n-hexyl phosphate, N,N-diethylcaprylamide, and the like. In addition to these high boiling point solvents, it is advantageous to use an auxiliary solvent having a low boiling point (not higher than 200° C.) in order to assist the dissolution of the couplers. Examples of such compounds are propylene carbonate, ethyl acetate, butyl acetate, cyclohexanol, tetrahydrofuran, cyclohexanone, etc.

A surface active agent can be advantageously used to aid in finely dispersing the solvents in a hydrophilic colloid employed in the photographic emulsion used in the present invention. Diffusion resistant couplers having a carboxylic acid group or a sulfonic acid group together with a ballast group in the molecule are soluble in a neutral or weakly alkaline aqueous solution. Such an aqueous solution can be added to the photographic emulsion used in the present invention.

The coupler of this invention is generally present in the light-sensitive photographic material in an amount of about 10 to 1,500 g, per mol of silver halide. However, this amount can be varied depending on the purpose of use.

The coupler of the present invention can be employed in various silver halide light-sensitive materials, for example, color negative films, color positive films, color reversal films, color papers, and various other color light-sensitive materials.

The coupler of the present invention can be used in a known multilayer structure of a multilayer color light-sensitive material, for example, those described in U.S. Pat. Nos. 3,726,681 and 3,516,831, British Pat. Nos. 818,687 and 923,045. The coupler of this invention can also be used in the method described in Japanese Patent Application No. 5179/1975 and the method in which the coupler is used together with a DIR compound as described in German Patent Application (OLS) No. 2,322,165 and U.S. Pat. No. 3,703,375.

To increase the stability of the color photographic images formed, it is advantageous for the light-sensitive material of the present invention to contain a p-substituted phenol derivative, e.g., a hydroquinone derivative, in an emulsion layer thereof or an adjacent layer thereto. Particularly preferred p-substituted phenol derivatives are those described in U.S. Pat. Nos. 2,360,290, 2,418,613, 2,675,314, 2,710,801, 2,728,659, 2,732,300, 2,735,765, 2,816,028, 3,457,079 and 3,069,262, Japanese Patent Publication No. 13496/1968, U.S. Pat. No. 2,735,765, Japanese Patent Application (OPI) No. 4738/1972, U.S. Pat. Nos. 3,432,300, 3,573,050, 3,574,627 and 3,764,337.

The light-sensitive material containing the coupler of the present invention can contain an ultraviolet absorbing agent as described, for example, in U.S. Pat. Nos. 3,250,617 and 3,253,921, in an emulsion layer or an adjacent layer thereto to stabilize the dye images formed.

The support for the color light-sensitive material of the present invention can be a cellulose acetate film, a cellulose acetate butyrate film, a polystyrene film, a polyethylene terephthalte film, a laminate of these films, a glass, a paper, a paper coated or laminated with baryta or a polymer of an α-olefin having 2 to 10 carbon atoms, such as polyethylene, polypropylene, an ethylene-butene copolymer, etc.

The photographic light-sensitive material containing the coupler of the present invention can be processed, after exposure, using known methods including basically a color development step, a bleaching step and a fixing step. Each step can be conducted separately or two or more steps can be carried out as one step using a processing solution which has the capability of accomplishing each of these steps. For example, the use of a bleach-fixing solution is one example of such a combination. If desired, the processing can include other steps, such as a prehardening, a neutralization, a first development (black-and-white development), an image stabilizing, a water washing, etc. The processing temperature used sometimes is below about 18° C. but often advantageously is above about 18° C. In particular, the temperature generally ranges from about 20° to about 60° C. In case of a rapid processing, a range from about 35° to about 60° C. is suitable.

A suitable color developer solution which can be used is an alkaline aqueous solution having a pH of about 8 or above, and particularly 9 to 12, which contains a color developing agent. Preferred examples of color developing agents are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-3-methyl-N-ethyl-N-β-methoxyethylaniline, etc. In addition, the compounds described in U.S. Pat. Nos. 2,193,015 and 2,592,364, Japanese Patent Application (OPI) No. 64933/1973 and L. F. A. Mason, *Photographic Processing Chemistry*, pages 226 to 229, Focal Press, London (1966), can be used.

The processing of the light-sensitive material containing the coupler of the present invention can be carried out in a color development step even in the presence of a competing coupler, such as citrazinic acid, etc., without practical damage.

After the color development step, the light-sensitive material of the present invention is subjected to a bleaching in a conventional manner. The bleaching can be carried out separately or simultaneously with fixing. In the latter case, a fixing agent is added to a bleaching solution to produce a bleach-fixing bath. Suitable bleaching agents, for example, include a ferricyanide, a bichromate, a complex salt of a polyvalent metal cation, such as iron (III), cobalt (III), etc., and an organic acid, for example, a metal complex salt of an aminopolycarboxylic acid, such as ethylenediamine tetraacetic acid, nitrilotriacetic acid, diaminopropanol tetraacetic acid, etc., citric acid, tartaric acid, malic acid, etc., can be used. This processing solution can also contain a bleaching accelerating agent as described in U.S. Pat. Nos. 3,042,520 and 3,241,966, Japanese Patent Publication Nos. 8506/1970 and 8836/1970, etc., and various other additives.

The coupler of the present invention can be used for light-sensitive photographic materials having a low silver content wherein the amount of silver halide in the emulsion is from about one half to about one hundredth of that present in conventional light-sensitive materials. It is possible to obtain a satisfactory color image in such color light-sensitive materials having a low silver halide content by employing an image-forming process which comprises a color intensification using a peroxide, a cobalt complex salt or sodium chlorite, for example, as described in German Patent Application (OLS) No. 2,357,694, U.S. Pat. Nos. 3,674,490 and 3,761,265, German Patent Application (OLS) Nos. 2,044,833, 2,056,359, 2,056,360, 2,226,770, Japanese Patent Application (OPI) Nos. 9728/1973 and 9729/1973, etc.

The couplers used in the present invention are characterized by the anilide ring of an α-(aliphatic or aromatic acyl)acetanilide being substituted with a sulfonamido group or a sulfamoyl group and by one of the hydrogen atoms on the carbon atoms of the α-position being substituted with a nitrogen atom which forms a heterocyclic compound. Couplers in which the anilide ring is substituted with a sulfonamido group or a sulfamoyl group but not substituted with a nitrogen atom which forms a heterocyclic group at the α-position, or couplers in which a nitrogen atom which forms a heterocyclic group is present at the α-position but the anilide ring is substituted with a group other than a sulfonamido group or a sulfamoyl group are known. However, the couplers of the present invention can be distinguished from these couplers and are novel compounds.

The yellow dye-forming couplers of the present invention are 2-equivalent couplers having superior coupling reactivity and the amount of silver halide present in a light-sensitive material can be reduced when they are used. Thus, these characteristics lead to the ability to reduce the production cost of the light-sensitive material as well as improve the sharpness of the image by reducing light scattering in the emulsion layer.

The couplers of the present invention not only have high coupling reactivity but also provide dye images of improved graininess and, thus, they are suitable for use, in particular, in a high speed light-sensitive material.

The couplers of the present invention do not cause a reduction of the density to occur even when they are treated with a developer solution containing a competing coupler, such as citrazinic acid. Thus, they are particularly suitable for use in an uppermost blue-sensitive silver halide emulsion layer of a color reversal light-sensitive material.

Further, color photographic light-sensitive materials containing the couplers of the present invention are particularly suitable for rapid processing at a high temperature such as at about 30° C. or higher, since the couplers of the present invention have the above-described properties.

Moreover, the couplers of the present invention can be used to obtain yellow dye images having superior stability and, thus, they can be suitably used in photographic materials which must be stored for a long period of time.

Furthermore, the couplers of the present invention are particularly suitable for the so-called oil-protect dispersing method in which couplers are dissolved in a high boiling organic solvent or in a low boiling organic solvent and then the solution is dispersed in the photographic emulsion, since they are highly soluble in organic solvents.

The present invention is further illustrated by reference to the following examples. However, the present invention is not to be construed as being limited to these examples.

EXAMPLE 1

On a subbed cellulose triacetate support, the following layers were coated in the order shown to prepare Sample A.

First Layer (antihalation layer)

A 6% aqueous gelatin solution containing black colloidal silver (amount of silver: 50 g/kg) was coated at a dry thickness of 1 micron.

Second Layer (intermediate layer)

100 g of a dispersion, which was prepared by dissolving 100 g of 2,5-di-tert-octylhydroquinone in a mixture of 100 g of tricresyl phosphate and 200 g of ethyl acetate, mixing the solution with 1 kg of a 10% aqueous gelatin solution containing 1 g of potassium dodecylbenzenesulfonate and agitating vigorously the mixture using a high speed homogenizer, was mixed with 1 kg of a 6% aqueous gelatin solution, 50 ml of a 2% aqueous solution of 2-hydroxy-4,6-dichloro-s-triazine sodium salt was added thereto as a gelatin hardener and the mixture was coated at a dry thickness of 1 microns.

Third Layer (red-sensitive emulsion layer)

To 1 kg of a silver iodobromide emulsion containing 6.5 g of silver iodobromide (iodide content: 6.0 mol%) and 10 g of gelatin, there were added 200 ml of a 0.03% methanol solution of a spectral sensitizer [Compound (I)]

Compound (I)

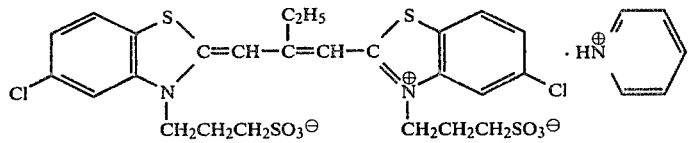

450 g of Dispersion (C-1) prepared in the manner as described below

| Dispersion (C-1) | | |
|---|---|---|
| (1) | 10% Aqueous Gelatin Solution | 1 kg |
| (2) | Cyan Coupler [Compound (II)] | 80 g |
|  | Ethyl Acetate | 110 ml |
|  | Tricresyl Phosphate | 65 ml |
|  | Sodium p-Dodecylbenzenesulfonate | 5 g |

Compound (II)

OH
[naphthalene]—CONH(CH$_2$)$_3$O—[benzene]—C$_5$H$_{11}$(t)
　　　　　　　　　　　　　　　　C$_5$H$_{11}$(t)

in which a mixture of (2) was dissolved at 60° C., the solution was added to (1) which was maintained at 60° C. and the mixture was vigorously agitated with a high speed homogenizer to prepare Dispersion (C-1), and 50 ml of a 2% aqueous solution of 2-hydroxy-4,6-dichloro-s-triazine sodium salt as a gelatin hardener and the mixture was coated in a silver coated amount of 20 mg/100 cm$^2$.

Fourth Layer (intermediate layer)

Same as the Second Layer.

Fifth Layer (green-sensitive emulsion layer)

To 1 kg of a silver iodobromide emulsion as described for the Third Layer, there were added 180 ml of a 0.03% methanol solution of a spectral sensitizer [Compound (III)]

Compound (III)

[benzoxazole]—C=CH—C(C$_2$H$_5$)=CH—C—[benzoxazole]
      |                              |
CH$_2$CH$_2$SO$_3$H              CH$_2$CH$_2$SO$_3$H 300 g of Dispersion (M-1) prepared in the manner as described below

| Dispersion (M-1) | | |
|---|---|---|
| (1) | 10% Aqueous Gelatin Solution | 1 kg |
| (2) | Magenta Coupler [Compound (IV)] | 60 g |
|  | Ethyl Acetate | 110 ml |
|  | Tricresyl Phosphate | 65 ml |
|  | Sodium p-Dodecylbenzenesulfonate | 5 g |

Compound (IV)

(t)C$_5$H$_{11}$—[benzene]—OCH$_2$CONH—[benzene]—CONH—C——CH$_2$
　　　C$_5$H$_{11}$(t)　　　　　　　　　　　　　　‖　　|
　　　　　　　　　　　　　　　　　　　　　　　　N　　C=O
　　　　　　　　　　　　　　　　　　　　　　　　　＼N／
　　　　　　　　　　　　　　　　　　　　　　　　Cl—[benzene]—Cl
　　　　　　　　　　　　　　　　　　　　　　　　　　　Cl in which Dispersion (M-1) was prepared in the same manner as Dispersion (C-1) and 50 ml of a 2% aqueous solution of 2-hydroxy-4,6-dichloro-s-triazine sodium salt as a gelatin hardener and the mixture was coated in a silver coated amount of 20 mg/100 cm$^2$.

Sixth Layer (yellow filter layer)

To 1 kg of a 6% aqueous gelatin solution containing 8 g of a Carey-Lea type yellow colloidal silver, 50 ml of a 2% aqueous solution of 2-hydroxy-4,6-dichloro-s-triazine sodium salt was added and the mixture was coated at a dry thickness of 2 microns.

Seventh Layer (blue-sensitive emulsion layer)

To 1 kg of a silver iodobromide emulsion containing 6.5 g of silver iodobromide (iodide content: 7 mol%) and 10 g of gelatin, there were added 800 g of Dispersion (Y-1) prepared in the manner as described below

| Dispersion (Y-1) | | |
|---|---|---|
| (1) | 10% Aqueous Gelatin Solution | 1 kg |
| (2) | Yellow Coupler [Compound (1)] | 100 g |
|  | Ethyl Acetate | 120 ml |
|  | Tricresyl Phosphate | 65 ml |
|  | Sodium p-Dodecylbenzenesulfonate | 5 g | in which Dispersion (Y-1) was prepared in the same manner as Dispersion (C-1) and 50 ml of a 2% aqueous solution of 2-hydroxy-4,6-dichloro-s-triazine sodium salt and the mixture was coated in a silver coated amount of 1.0 g/m$^2$.

Eighth Layer (gelatin protective layer)

To 1 kg of a 6% aqueous gelatin solution, 50 ml of a 2% aqueous solution of 2-hydroxy-4,6-dichloro-s-triazine sodium salt was added and the mixture was coated at a dry thickness of 1 micron.

Samples B, C, D, E, F, G and H were prepared in the same manner as described above for Sample A except the couplers and the coated amount of silver in the Seventh Layer as shown in Table 1 below were used. The molar ratio of silver/coupler in the Seventh Layer in Samples B, C, D, E, F, G and H was same as that in Sample A.

Table 1

| Sample No. | Coupler No. | Amount of Silver Coated (g/100 cm$^2$) |
|---|---|---|
| A | Coupler (1)* | 1.0 |
| B | Coupler (3)* | 1.0 |
| C | Coupler (11)* | 1.0 |
| D | Compound (A) | 1.2 |
| E | Compound (B) | 1.2 |
| F | Compound (C) | 1.0 |
| G | Compound (D) | 1.1 |
| H | Compound (E) | 1.2 |

*Present Invention

Compound (A)
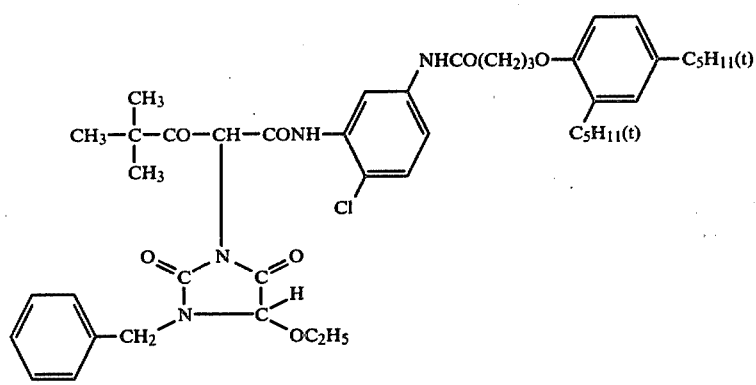
Compound (B)
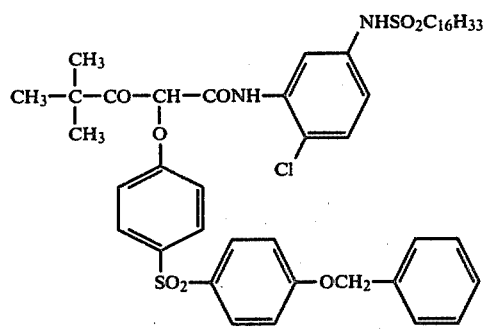
Compound (C)
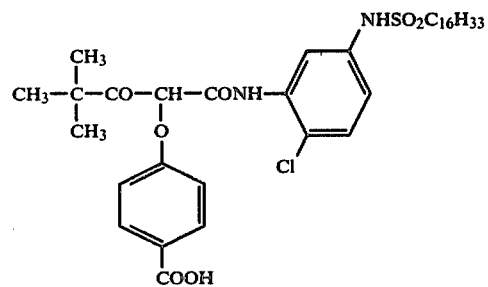
Compound (D)
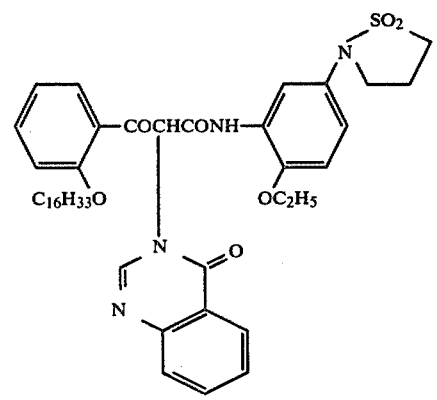

Compound (E) -continued

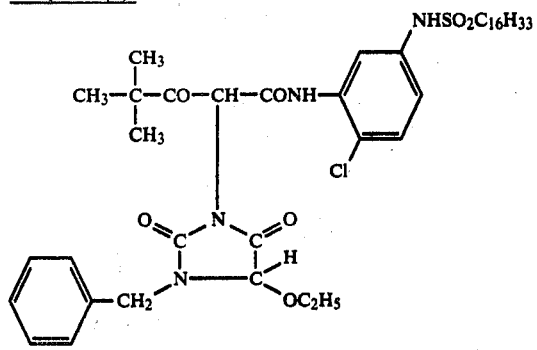

Samples A, B, C, D, E, F, G and F were exposed to white light through a step wedge of a step density difference of 0.15 and were development processed in the following manner.

| Processing Step | Temperature (°C.) | Time (min) |
|---|---|---|
| Color Development | 38 | 3 |
| Stopping | 38 | 1 |
| Washing | 38 | 1 |
| Bleaching | 38 | 2 |
| Washing | 38 | 1 |
| Fixing | 38 | 2 |
| Washing | 38 | 1 |
| Stabilizing | 38 | 1 |

The compositions of the processing solutions used were as follows.

| Color Developer Solution | |
|---|---|
| Sodium Hydroxide | 2 g |
| Sodium Sulfite | 2 g |
| Potassium Bromide | 0.4 g |
| Sodium Chloride | 1 g |
| Borax | 4 g |
| Hydroxylamine Sulfate | 2 g |
| Disodium Ethylenediamine Tetraacetate (dihydrate) | 2 g |
| 4-Amino-3-methyl-N-ethyl-N-(β-hydroxyethyl)aniline Monosulfate | 4 g |
| Water to make | 1 l |

| Stopping Solution | |
|---|---|
| Sodium Thiosulfate | 10 g |
| Ammonium Thiosulfate (70% aq. soln.) | 30 ml |
| Acetic Acid | 30 ml |
| Sodium Acetate | 5 g |
| Potassium Alum | 15 g |
| Water to make | 1 l |

| Bleaching Solution | |
|---|---|
| Sodium Iron (III) Ethylenediamine Tetraacetate (dihydrate) | 100 g |
| Potassium Bromide | 50 g |
| Ammonium Nitrate | 50 g |
| Boric Acid | 5 g |
| Aqueous Ammonia for adjusting pH to 5.0 | |
| Water to make | 1 l |

| Fixing Solution | |
|---|---|
| Sodium Thiosulfate | 150 g |
| Sodium Sulfite | 15 g |
| Borax | 12 g |
| Glacial Acetic Acid | 15 ml |
| Potassium Alum | 20 g |
| Water to make | 1 l |

| Stabilizing Bath | |
|---|---|
| Boric Acid | 5 g |
| Sodium Citrate | 5 g |
| Sodium Metaborate (tetrahydrate) | 3 g |
| Potassium Alum | 15 g |
| Water to make | 1 l |

The optical density of each sample thus-processed was measured through a blue filter and fog, sensitivity and gamma of the yellow dye image and graininess of the image of an optical density of 0.5 were determined. The sensitivity was shown as a relative value of the exposure amount required to obtain a density of fog+0.2 using Sample A as a control. The gamma was calculated using the following relationship.

$$\text{Gamma} = [(\log E)_D = \text{fog} + 0.7 - (\log E)_D = \text{fog} + 0.2]/0.5$$

wherein $(\log E)_D$ represents the logarithm of the exposure amount required to obtain a density of D. The graininess was evaluated using Selwin's G value (*Phot. J.*, Vol. 79, p. 513 (1939)) in an image of an image density of 0.5. The smaller the G value is, the better is the graininess.

Further, in order to evaluate the sharpness, the sample was exposed to white light through a black and white sharp contrast image and a filter having a repeating pattern of straight lines (frequency: 20 lines/mm) which had the same density difference as the above-described black and white image and then processed in the same manner as described above. The optical density of the sample thus-processed was measured through a green filter or a red filter using a microdensitometer and the squarewave response function (designated S.R.F. hereinafter) was determined as follows.

$$S.R.F. = \frac{D_{max} - D_{min}}{\Delta D}$$

wherein $D_{max}$ represents the maximum value of the microdensity of a line in a repeating pattern of straight lines, $D_{min}$ represents the minimum value of the microdensity of a line in a repeating pattern of straight lines, and ΔD represents the difference between the maximum density and the minimum density of the sharp contrast image. The greater the value of S.R.F. is, the better is the sharpness.

The fog, sensitivity, gamma, G value and S.R.F. value of each sample are shown in Table 2 below.

Table 2

Comparison of Properties of Samples A, B, C, D, E, F, G and H

| Sample No. | Fog | Sensi- tivity | Gamma | G Value | S.R.F. G Filter | S.R.F. R Filter |
|---|---|---|---|---|---|---|
| A | 0.14 | 110 | 0.85 | 0.54 | 0.62 | 0.32 |
| B | 0.13 | 111 | 0.87 | 0.53 | 0.61 | 0.34 |
| C | 0.14 | 112 | 0.89 | 0.54 | 0.62 | 0.33 |
| D | 0.13 | 77 | 0.77 | 0.55 | 0.48 | 0.25 |
| E | 0.14 | 80 | 0.79 | 0.55 | 0.49 | 0.26 |
| F | 0.24 | 100 | 0.84 | 0.64 | 0.55 | 0.31 |
| G | 0.14 | 79 | 0.78 | 0.55 | 0.50 | 0.26 |
| H | 0.14 | 97 | 0.80 | 0.55 | 0.55 | 0.31 |

From the results shown above, it is apparent that Samples A, B and C containing the coupler of the present invention have almost the same fog and graininess, high sensitivity and gamma, and a superior sharpness of the magenta and cyan color images in comparison with comparison Samples D, E and H even though the silver coated amount in the Seventh Layer of the A, B, C is smaller by about 20% of than that of the D, E, H. Also, comparison Sample F has a large fog and an inferior graininess in comparison with Samples A, B and C according to the present invention. Further, Samples A, B and C according to the present invention have not only superior sensitivity and gamma but also a superior sharpness of the magenta and cyan dye images in comparison with comparison Sample G.

EXAMPLE 2

On a subbed cellulose triacetate support, the following emulsion layers and subsidiary layers were coated in the order shown below to prepare Sample J.

First Layer (red-sensitive emulsion layer)

350 g of a dispersion which was prepared by dissolving 100 g of 1-hydroxy-2-[γ-(2,4-di-tert-amyl-phenoxy)-butyl]naphthamide, as a cyan coupler, in a mixture of 100 ml of dibutyl phthalate and 100 ml of ethyl acetate, mixing the solution with 1 kg of a 10% aqueous gelatin solution and agitating with high speed was mixed with 1 kg of a red-sensitive silver iodobromide emulsion containing 50 g of silver, 60 g of gelatin and 6 mol% of iodide, and the mixture was coated at a dry thickness of 3 microns.

Second Layer (intermediate layer)

100 g of a dispersion which was prepared in the same manner as the dispersion used in the First Layer except using 2,5-di-tert-amylhydroquinone in place of the cyan coupler was mixed with 1 kg of a 5% aqueous gelatin solution and the mixture was coated at a dry thickness of 1 micron.

Third Layer (green-sensitiv- emulsion layer)

500 g of a dispersion which was prepared by dissolving 100 g of 1-(2,4,6-trichlorophenyl)-3-[3-(2,4-di-tert-amylphenoxyacetamido)benzamido]-5-pyrazolone, as a magenta coupler, in a mixture of 100 ml of tricresyl phosphate and 100 ml of ethyl acetate, mixing the solution with 1 kg of a 10% aqueous gelatin solution and agitating with high speed was mixed with 1 kg of a green-sensitive silver iodobromide emulsion containing 50 g of silver, 60 g of gelatin and 7 mol% of iodide, and the mixture was coated at a dry thickness of 4.5 microns.

Fourth Layer (yellow filter layer)

An emulsion containing yellow colloidal silver was coated at a dry thickness of 1 micron at a silver coating amount of 0.1 g/m$^2$.

Fifth Layer (blue-sensitive emulsion layer)

940 g of a dispersion which was prepared in the same manner as the dispersion used in the First Layer except using Coupler (1) of the present invention, as a yellow coupler, in place of the cyan coupler was mixed with 1 kg of a blue-sensitive silver iodobromide emulsion containing 60 g of silver, 60 g of gelatin and 5 mol% of iodide, and the mixture was coated at a dry thickness of 3.5 microns.

Sixth Layer (protective layer)

A 5% aqueous gelatin solution was coated at a dry thickness of 1 micron.

Samples K, L, M, N and O were prepared in the same manner as described for Sample J above except using 1,380 g of a dispersion each containing, as a yellow coupler, Coupler (3), Coupler (11), Compound (A), Compound (B) and Compound (E) as described in Example 1.

These samples were step-wise exposed to white light and were subjected to color reversal processing in the following manner.

| Processing Step | Temperature (°C.) | Time |
|---|---|---|
| Prehardening | 37 | 2 min 30 sec |
| Neutralization | 37 | 30 sec |
| First Development | 37 | 3 min |
| First Stopping | 37 | 30 sec |
| Washing | 37 | 1 min |
| Color Development | 37 | 3 min 30 sec |
| Second Stopping | 37 | 30 sec |
| Washing | 37 | 1 min |
| Bleaching | 37 | 2 min |
| Stain-Removing | 37 | 2 min |
| Fixing | 37 | 1 min |
| Washing | 37 | 1 min |

The compositions of the processing solutions used were as follows.

| Prehardening Solution | |
|---|---|
| Formaldehyde (37% aq. soln.) | 20 ml |
| Pyruvic Aldehyde (40%) | 20 ml |
| Sulfuric Acid | 2 ml |
| Sodium Sulfate | 100 g |
| Potassium Bromide | 2 g |
| Boric Acid | 5 g |
| Water to make | 1 l |

| Neutralization Solution | |
|---|---|
| Potassium Bromide | 20 g |
| Glacial Acetic Acid | 10 ml |
| Sodium Sulfate | 50 g |
| Sodium Hydroxide | 6 g |
| Glycine | 10 g |

-continued

Neutralization Solution

| | |
|---|---|
| Water to make | 1 l |

First Developer Solution

| | |
|---|---|
| Sodum Hexametaphosphate | 1.0 g |
| 1-Phenyl-3-pyrazolidone | 0.3 g |
| Sodium Sulfite | 50.0 g |
| Hydroquinone | 6.0 g |
| Sodium Carbonate (monohydrate) | 35.0 g |
| Potassium Bromide | 2.0 g |
| Potassium Thiocyanate | 1.0 g |
| Potassium Iodide (0.1% aq. soln.) | 10.0 ml |
| Water to make | 1 l |

First Stopping Solution and Second Stopping Solution

| | |
|---|---|
| Acetic Acid | 25 ml |
| Sodium Acetate | 3 g |
| Water to make | 1 l |

Color Developer Solution

| | |
|---|---|
| Sodium Hexametaphosphate | 1.0 g |
| Benzyl Alcohol | 6.0 ml |
| Sodium Sulfite | 5.0 g |
| Sodium Tertiary Phosphate | 40.0 g |
| Potassium Bromide | 0.2 g |
| Potassium Iodide (0.1% aq. soln.) | 10.0 ml |
| Sodium Hydroxide | 6.5 g |
| 4-Amino-3-methyl-N-ethyl-N-methanesulfonamidoethylaniline Sulfate | 10.0 g |
| Ethylenediamine | 8.0 ml |
| Citrazinic Acid | 1.2 g |
| Sodium Borohydride | 0.1 g |
| Water to make | 1 l |

Bleaching Solution

| | |
|---|---|
| Ferric Chloride (hexahydrate) | 200 g |
| Sodium Citrate (dihydrate) | 40 g |
| Potassium Ferricyanide | 100 g |
| Sodium Acetate | 40 g |
| Glacial Acetic Acid | 20 ml |
| Potassium Bromide | 30 g |
| Water to make | 1 l |

Fixing Solution

| | |
|---|---|
| Sodium Thiosulfate | 150 g |
| Sodium Acetate | 70 g |
| Sodium Sulfite | 10 g |
| Potassium Alum | 20 g |
| Water to make | 1 l |

The optical density of each sample thus-processed was measured through a blue-light filter, a green-light filter and a red-light filter. The maximum density and gamma value of each sample obtained are summarized below.

Table

| Comparison of Properties of Samples J, K, L, M, N and O | | |
|---|---|---|
| Sample No. | Maximum Density | Gamma Value |
| J | 3.62 | 2.11 |
| K | 3.59 | 2.10 |
| L | 3.64 | 2.14 |
| M | 2.84 | 1.66 |
| N | 3.39 | 1.95 |
| O | 3.03 | 1.75 |

From the results shown in the above table, it is apparent that the couplers of the present invention provide higher maximum density and gamma value in comparison with known couplers and that the activity of the coupler according to the present invention is extremely high.

While the invention has been described in detail and with reference to specific embodiments thereof, it will be apparent to one skilled in the art that various changes and modifications can be made therein without departing from the spirit and scope thereof.

What is claimed is:

1. A photographic silver halide emulsion containing a yellow dye-forming coupler represented by the following general formula (I):

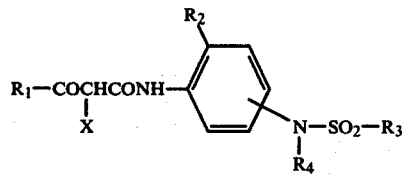

(I)

wherein $R_1$ represents an alkyl group or a monocyclic aryl group; $R_2$ represents a chlorine atom or a lower alkoxy group having 1 to 4 carbon atoms; $R_3$ and $R_4$, which may be the same or different, each represents a straight or branched chain alkyl group having 1 to 22 carbon atoms, a phenoxyalkyl group having 7 to 32 carbon atoms, a monocyclic aralkyl group having 7 to 32 carbon atoms, a phenyl group or a substituted phenyl group; and X is selected from the group consisting of groups represented by the following general formula

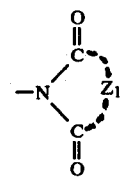

(III)

wherein $Z_1$ represents the non-metallic atoms necessary to form together with the

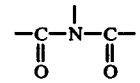

moiety a 5-membered ring or a 6-membered ring,

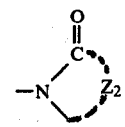

(IV)

wherein $Z_2$ represents the non-metallic atoms necessary to form together with the

moiety an unsaturated 5-membered ring or an unsaturated 6-membered ring, or

 (V)

wherein $Z_3$ represents the non-metallic atoms necessary to form together with

an imidazole ring, a triazole ring or a tetrazole ring.

2. The photographic silver halide emulsion as claimed in claim 1, wherein $R_1$ represents a branched chain alkyl group having 3 to 8 carbon atoms, a cyclic alkyl group having 3 to 10 carbon atoms, a phenyl group, a 2- or 4-alkylphenyl group wherein the alkyl moiety has 1 to 5 carbon atoms or a 2- or 4-alkoxyphenyl group wherein the alkoxy moiety has 1 to 5 carbon atoms, and $R_2$ represents a chlorine atom or a lower alkoxy group having 1 to 4 carbon atoms.

3. The photographic silver halide emulsion as claimed in claim 2, wherein $R_1$ represents a tert-butyl group.

4. The photographic silver halide emulsion as claimed in claim 1, wherein said yellow dye-forming coupler is represented by the following general formula (VII):

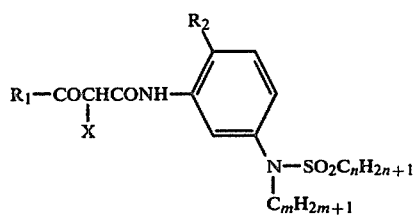 (VII)

wherein $R_1$, $R_2$ and X have the same meaning as defined in claim 1 and m and n each represents an integer of 1 to 18.

5. A photographic light-sensitive material which comprises a support having thereon the photographic silver halide emulsion as claimed in claim 1.

6. A photographic light-sensitive material which comprises a support having thereon a red-sensitive silver halide emulsion layer containing a cyan dye-forming coupler, a green-sensitive silver halide emulsion layer containing a magenta dye-forming coupler and a blue-sensitive silver halide emulsion layer comprising the photographic silver halide emulsion as claimed in claim 1.

7. A method for formation of color photographic images which comprises developing an image-wise exposed photographic light-sensitive material as claimed in claim 5 in an aqueous alkaline solution containing a primary aromatic amine color developing agent.

8. A method for formation of color photographic images which comprises developing an image-wise exposed photographic light-sensitive material as claimed in claim 6 in an aqueous alkaline solution containing a primary aromatic amine color developing agent.

9. A method for formation of color photographic images which comprises developing an image-wise exposed photographic light-sensitive material comprising a support having thereon at least one silver halide emulsion layer with a primary aromatic amine color developing agent in the presence of a yellow dye-forming coupler represented by the following general formula (I):

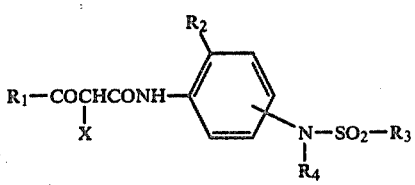 (I)

wherein $R_1$ represents an alkyl group or a monocyclic aryl group; $R_2$ represents a chlorine atom or a lower alkoxy group having 1 to 4 carbon atoms; $R_3$ and $R_4$, which may be the same or different, each represents a straight chain or branched chain alkyl group having 1 to 22 carbon atoms, a phenoxyalkyl group having 7 to 32 carbon atoms, a monocyclic aralkyl group having 7 to 32 carbon atoms, a phenyl group or a substituted phenyl group; and X is selected from the group consisting of groups represented by the following general formulae (III) to (V):

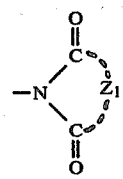 (III)

wherein $Z_1$ represents the non-metallic atoms necessary to form together with the

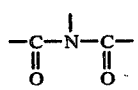

moiety a 5-membered ring or a 6-membered ring,

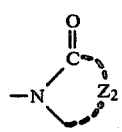 (IV)

wherein $Z_2$ represents the non-metallic atoms necessary to form together with the

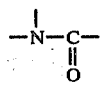

moiety an unsaturated 5-membered ring or an unsaturated 6-membered ring, or

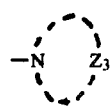 (V)
wherein $Z_3$ represents the non-metallic atoms necessary to form together with
an imidazole ring, a triazole ring or a tetrazole ring.
* * * * *